United States Patent
Li (10) Patent No.: US 10,621,432 B2
(45) Date of Patent: Apr. 14, 2020

(54) METHODS FOR ACQUIRING INFORMATION USING BIOLOGICAL FEATURE, AND TERMINAL AND BACKGROUND SERVER

(71) Applicant: TENDYRON CORPORATION, Beijing (CN)

(72) Inventor: Dongsheng Li, Beijing (CN)

(73) Assignee: TENDYRON CORPORATION, Beijing (CN)

( * ) Notice: Subject to any disclaimer, the term of this patent is extended or adjusted under 35 U.S.C. 154(b) by 139 days.

(21) Appl. No.: 16/060,004

(22) PCT Filed: Nov. 29, 2016

(86) PCT No.: PCT/CN2016/107586
§ 371 (c)(1),
(2) Date: Jun. 6, 2018

(87) PCT Pub. No.: WO2017/097136
PCT Pub. Date: Jun. 15, 2017

(65) Prior Publication Data
US 2018/0357466 A1    Dec. 13, 2018

(30) Foreign Application Priority Data
Dec. 10, 2015    (CN) .......................... 2015 1 0917162

(51) Int. Cl.
*G06T 7/00*    (2017.01)
*G06T 7/73*    (2017.01)
(Continued)

(52) U.S. Cl.
CPC .......... *G06K 9/0061* (2013.01); *A61B 3/0008* (2013.01); *A61B 3/112* (2013.01);
(Continued)

(58) Field of Classification Search
CPC ......... A61B 3/0008; A61B 3/112; A61B 3/14; G06T 2207/10152; G06T 2207/30041; G06T 7/0016; G06T 7/74
See application file for complete search history.

(56) References Cited

U.S. PATENT DOCUMENTS

2015/0116665 A1*  4/2015  Finkel ................... A61B 3/112
                                                            351/246
2015/0245766 A1*  9/2015  Rennaker ............... A61B 3/112
                                                            351/210
(Continued)

FOREIGN PATENT DOCUMENTS

CN    1361894 A    7/2002
CN    103544420 A    1/2014
(Continued)

OTHER PUBLICATIONS

International Patent Application No. PCT/CN2016/107586; Int'l Written Opinion and the Search Report; dated Feb. 14, 2017; 7 pages.

*Primary Examiner* — David Bilodeau
(74) *Attorney, Agent, or Firm* — BakerHostetler (57) ABSTRACT

The present invention provides methods, systems and equipment for acquiring and extracting information using a biological feature. The method for acquiring information using a biological feature—includes: acquiring first data by a terminal; controlling, by the terminal, a light source to generate an intensity-variable light signal according to the first data, and projecting the intensity-variable light signal on an iris; acquiring, by the terminal, first iris information at least comprising first iris contraction information, in which the first iris contraction information is generated by the iris according to the intensity-variable light signal and comprises a first iris contraction activity; acquiring, by the terminal, second iris information at least comprising second
(Continued)

iris contraction information; and extracting, by the terminal, second data from the second iris contraction information according to a preset rule.

16 Claims, 4 Drawing Sheets

(51) Int. Cl.
  *G06K 9/20* (2006.01)
  *A61B 3/00* (2006.01)
  *A61B 3/14* (2006.01)
  *G06K 9/00* (2006.01)
  *G06Q 20/38* (2012.01)
  *A61B 3/11* (2006.01)
  *G06K 9/46* (2006.01)

(52) U.S. Cl.
  CPC ............ *A61B 3/14* (2013.01); *G06K 9/00604* (2013.01); *G06K 9/2027* (2013.01); *G06K 9/4661* (2013.01); *G06Q 20/38* (2013.01); *G06T 7/0016* (2013.01); *G06T 7/74* (2017.01); *G06T 2207/10016* (2013.01); *G06T 2207/10152* (2013.01); *G06T 2207/30041* (2013.01)

(56) References Cited

U.S. PATENT DOCUMENTS

| | | | |
|---|---|---|---|
| 2017/0143241 A1* | 5/2017 | McBain | B64D 45/0015 |
| 2017/0231490 A1* | 8/2017 | Toth | A61B 5/40 600/558 |
| 2017/0251366 A1* | 8/2017 | Perna | A61B 3/1216 |
| 2017/0323167 A1* | 11/2017 | Mapen | G06K 9/00604 |
| 2018/0173986 A1* | 6/2018 | Gousev | G06T 7/62 |

FOREIGN PATENT DOCUMENTS

| | | |
|---|---|---|
| CN | 105931045 A | 9/2016 |
| WO | WO 2001/008056 A1 | 2/2001 |

* cited by examiner

METHODS FOR ACQUIRING INFORMATION USING BIOLOGICAL FEATURE, AND TERMINAL AND BACKGROUND SERVER

CROSS-REFERENCE TO RELATED APPLICATION

This application is a U.S. National phase application of International Application No. PCT/CN2016/107586, filed on Nov. 29, 2016, which claims priority to and benefits of Chinese Patent Application Serial No. 201510917162.6, titled "Methods, systems and equipment for acquiring and extracting information by utilizing biological features", filed with the State Intellectual Property Office of P. R. China on Dec. 10, 2015, the entire content of which is incorporated herein by reference.

FIELD

The present disclosure generally relates to a technology field of transferring information by utilizing a biological feature, and more particularly, to a method for acquiring and extracting information using a biological feature, and a terminal and a background server.

BACKGROUND

With a development of Internet technology, electronic commerce trade is wildly applied in human's lives. At present, when a user confirms content of a trade activity, the manner of inputting a password has a risk of being stolen for the user, such that a convenient method without inputting the trade in other devices by the user is required.

As an electronic trading process is performed via an open media, when the electronic commerce trade is performed, especially when price information such as an order form and an electronic check is sent via Internet, two parties of the trade may deny the content (such as amount and/or quantity) of the trade. Thus, a method for preventing the two parties of the trade from denying the trade content is required.

Moreover, in the electronic trading process, denying of a behavior by the two parties themselves (such as signing for something) may be unavoidable. For example, when signing for a package, it should be guaranteed that a signer cannot deny the behavior of signing for the package. Thus, a method for preventing the two parties of the trade from denying their own behaviors is required.

With an intensive study of an eye iris, it is well known that a human's eye consists of a sclera, an iris, a pupil and a retina. The iris is a circular part between the pupil and the sclera, including detail features such as interlaced spots, thread lets, coronary, stripes recesses and the like. Moreover, the iris formed after a fetal development stage will remain unchanged in a whole life period. These features cause a uniqueness of the iris. Meanwhile, irises having different features may be contracted when a light stimulation occurs. The light stimulation with a specific frequency will cause a regular contraction for the iris. Therefore, how to use a biological feature to prevent the two parties from denying the trade content or the trade behavior is a technical problem required to be solved at present.

SUMMARY

The present disclosure aims to solve at least one of the above problems.

A main objective of the present disclosure is to provide a method for acquiring information using a biological feature.

Another objective of the present disclosure is to provide a method for extracting information using a biological feature.

Another objective of the present disclosure is to provide a terminal.

Another objective of the present disclosure is to provide a background server.

Another objective of the present disclosure is to provide a system for extracting information using a biological feature.

In order to achieve the above objectives, technical solutions of the present disclosure are achieved as follows.

An aspect of the present disclosure provides a method for acquiring information using a biological feature, including: acquiring first data by a terminal; controlling, by the terminal, a light source to generate an intensity-variable light signal according to the first data, and projecting the intensity-variable light signal on an iris; acquiring, by the terminal, first iris information at least including first iris contraction information, in which the first iris contraction information is generated by the iris according to the intensity-variable light signal and includes a first iris contraction activity; acquiring, by the terminal, second iris information at least including second iris contraction information; and extracting, by the terminal, second data from the second iris contraction information according to a preset rule.

Another aspect of the present disclosure provides a method for extracting information using a biological feature, including: receiving, by a background server, first iris information sent by a terminal, in which the first iris information is acquired by the terminal using the method mentioned above; and extracting, by the background server, the first data from the first iris contraction information according to the preset rule.

Another aspect of the present disclosure provides a terminal, including: a first acquiring component, configured to acquire first data; a light source generating component, configured to generate a light source; a controlling component, configured to control the light source to generate an intensity-variable light signal according to the first data; an output component, configured to project the intensity-variable light signal on an iris, in which the first acquiring component is further configured to acquire first iris information at least including first iris contraction information, and the first iris contraction information is generated by the iris according to the intensity-variable light signal and includes a first iris contraction activity. The terminal further includes a second acquiring component, configured to acquire second iris information at least including second iris contraction information; and an extracting component, configured to extract second data from the second iris contraction information according to a preset rule.

Another aspect of the present disclosure provides a background server. The background server may include: a receiving component, configured to receive first iris information sent by a terminal, in which the first iris information at least includes first iris contraction information; and an extracting component, configured to extract first data from the first iris contraction information according to a preset rule.

Another aspect of the present disclosure also provides a system for extracting information using a biological feature. The system includes the terminal mentioned above and the background server mentioned above.

BRIEF DESCRIPTION OF THE DRAWINGS

To describe the technical solutions in the embodiments of the present disclosure more clearly, the accompanying drawings required for describing the embodiments are introduced briefly in the following. Obviously, the accompanying drawings in the following description are only some embodiments of the present disclosure, and persons of ordinary skill in the art may also derive other drawings from these accompanying drawings without creative efforts.

DETAILED DESCRIPTION

The technical solutions in the embodiments of the present disclosure are clearly and completely described in the following with reference to the accompanying drawings in the embodiments of the present disclosure. Obviously, the embodiments in the following description are merely a part rather than all of the embodiments of the present disclosure. Based on the embodiments of the present disclosure, all other embodiments obtained by persons of ordinary skill in the art without creative efforts shall fall within the protection scope of the present disclosure.

In the following, embodiments of the present disclosure will be described in detail with reference to the accompanying drawings.

First Embodiment

Figure 1:
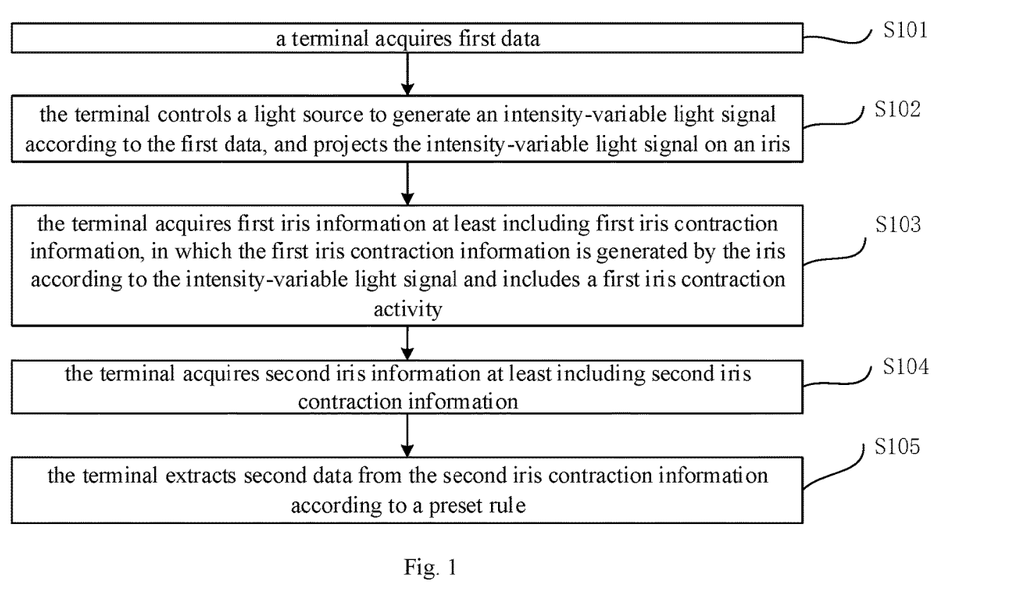
FIG. 1 is a flow chart of a method for acquiring information using a biological feature provided by a first Embodiment of the present disclosure.

FIG. 1 is a flow chart of a method for acquiring information using a biological feature provided by the present embodiment. As shown in FIG. 1, the method includes following acts (S101-S103).

At block S101, a terminal acquires first data.

In this embodiment, the terminal may include any of: a smart phone, a tablet, a laptop, a PC, an electronic signature token (such as USB-keys developed by Industrial and Commercial Bank of China or Agricultural Bank of China), or a wearable device and the like.

In this embodiment, the first data is data required to be represented by an iris contraction activity. The first data may be any one of a time, a site, a character (such as a name), order information, trade information, signature data and any combination thereof, or may be a characteristic value acquired by performing computation on any one of the time, the site, the character, the order information, the trade information, the signature data and any combination thereof, or may be data generated by combining the characteristic value with any one of the time, the site, the character, the order information, the trade information, the signature data and any combination thereof. Any data represented by the iris contraction activity may be determined as the first data, which will not be limited in this embodiment. Various methods may be used to compute the characteristic value. For example, N-digit data is to be computed in the present disclosure, first X digits in the data may be selected as the characteristic value, where $1 \leq X \leq N$. Alternatively, Y digits may be computed as the characteristic value by hash algorithm or MAC algorithm, where $1 \leq Y \leq N$. Efficiency may be improved by selecting the characteristic value as the first data, such that a light stimulation to the iris may be reduced when there are too many digits in the first data.

As an alternative implementation, the first data may also be numbers of different events. For example, in an event of fetching an express delivery, the first data may be 1; in an event of shopping, the first data may be 2; in an event of hailing a cab, the first data may be 3. Of course, the first data may be numbers of application scenes of different events, in which the number may be represented by a number corresponding to event plus a number corresponding to application scene. For example, in an application scene of fetching an SF express delivery, the first data may be 11; in an application scene of fetching a YTO express delivery, the first data may be 12; in an application scene of fetching a ZTO express delivery, the first data may be 13; in an application scene of shopping at CapitaMall, the first data may be 21; in an application scene of shopping at Wu-Mart, the first data may be 22; in an application scene of shopping at Wal-Mart, the first data may be 23. In a case of numbering different events and/or application scenes with digits, it is convenient to confirm the kind of event on which operations including confirming, signing-for and the like are performed by using the first data.

In this embodiment, the terminal may generate the first data by the terminal itself. For example, the first data may be generated by an input of the terminal. Of course, the terminal may acquire the first data by scanning a QR code or a bar code. Acquiring the first data in a manner of scanning may reduce complexity of inputting operations. Preferably, the terminal may acquire the first data by receiving data sent by the background server. Acquiring the first data by receiving data sent by the background server may avoid malicious tempering with the first data.

At block S102, the terminal controls a light source to generate an intensity-variable light signal according to the first data, and projects the intensity-variable light signal on an iris.

In this embodiment, the light source may be infrared light, visible light or white light. The light source causing an iris contraction and dilation falls within the protection scope of the present disclosure. Preferably, a flashlight configured on a terminal such as a mobile phone may be regarded as the light source, in this case no additional light source generating device is needed for the terminal such as the mobile phone.

The terminal may control the light source to generate the intensity-variable light signal according to the first data by at least one of following manners.

In a first manner, the terminal modulates the first data on the light source in a preset modulation mode, so as to generate the intensity-variable light signal.

Specifically, the first data may be represented as a modulation signal by binary data including "0" and "1". The light source may be regarded as a carrier signal. The modulation signal (the first data) may be modulated on the carrier signal in an intensity modulation mode to generate a modulated signal. An intensity of the carrier signal varies with the modulation signal. For example, the preset modulation mode may be represented as follows. "0" is represented by no light, "1" is represented by light. When the first data is "1001011010", a state of the modulated signal may be represented as "light, no light, no light, light, no light, light, light, no light, light, no light", and the modulated signal is the intensity-variable light signal. In addition, other modulation mode, for example, an amplitude modulation mode can be used as the preset modulation mode. Modulation modes allowing generating the intensity-variable light signal causing the iris contraction activity fall within the protection scope of the present disclosure. The intensity-variable light signal may be generated by modulating the first data on the light source, such that the iris may be stimulated. Furthermore, it is easy to generate the intensity-variable light signal by using the intensity modulation mode.

In a second manner, the terminal encodes the first data to generate an encoded signal of the first data, and modulates the encoded signal on the light source in a preset modulation mode, so as to generate the intensity-variable light signal.

Figure 2:
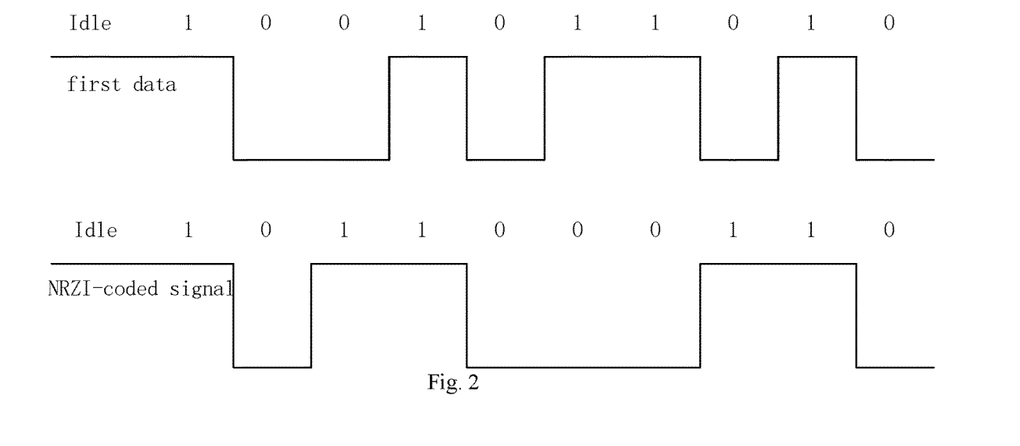
FIG. 2 is a schematic diagram of NRZI coding method provided by the first Embodiment of the present disclosure.

In this embodiment, the terminal may encode the first data via NRZI coding method. Specifically, an encoding principle of NRZI coding method may be described as follows. Logic "1" in the first data may be represented by an unchanged level, logic "0" in the first data may be represented by a flipped level. After the first data "1001011010" is encoded by using the NRZI coding method, an encoded signal "1011000110" may be generated, as shown in FIG. 2. It should be noted that, "Idle" illustrated in FIG. 2 represents a preset reference level signal. By encoding the first data via the NRZI coding method and controlling the light source to generate the intensity-variable light signal according to the encoded signal, the first data may be represented according to whether an iris state is changed. In addition, the encoding manner using which the terminal encodes the first data may be a ternary encoding method. When the first data is "1001011010", the encoded signal generated by encoding the first data using the ternary coding method may be "211022". The encoded signal represented by ternary data may be a numeric string containing "0", "1" and "2", which is regarded as a modulation signal, and the light source may be configured as a carrier signal. The encoded signal may be modulated on the carrier signal by an intensity modulation mode to generate a modulated signal. An intensity of the carrier signal may vary with the modulation signal. For example, the preset modulation mode may be represented as follows. "0" is represented by no light, "1" is represented by low light, and "2" is represented by high light. Light signals having different intensities may cause different contraction degrees of the iris. The first data may be represented by various iris states. Of course, other coding methods are also allowable, which is not limited in the present disclosure.

As an alternative implementation of the present embodiment, before the terminal controls the light source to generate the intensity-variable light signal according to the first data, the method further includes: controlling, by the terminal, the light source to generate a reference light signal according to reference data. The reference data may be pre-stored in the terminal, or may be generated after a negotiation between the terminal and the background server, which is not limited in the present embodiment. Any data having the function of reference data in the present embodiment falls within the protection scope of the present disclosure. The implementation that the terminal controls the light source to generate a reference light signal according to reference data is the same as the implementation that the terminal controls the light source to generate the intensity-variable light signal according to the first data, which will not be described in detail herein. The reference light signal generated by the light source according to the reference data may also be a flashing light signal. After the reference light signal is generated, the reference light signal is projected on the iris. The iris is stimulated by the reference light signal and reference iris contraction information may be generated, in which the reference iris contraction information includes a reference iris contraction activity. Specifically, the reference light signal is a flashing light signal. When there are lights, the iris is in a contraction state, and when there is no light, the iris is in a dilation state. With a constant flashing of the reference light signal, the iris contracts or dilates continuously such that the reference iris contraction activity is generated. The reference light signal generated by the light source controlled according to the reference data may stimulate iris to generate the reference iris contraction activity, and the reference iris contraction activity may be regarded as a reference to calibrate the iris contraction activity.

At block S103, the terminal acquires first iris information at least including first iris contraction information, in which the first iris contraction information is generated by the iris according to the intensity-variable light signal and includes a first iris contraction activity.

In this embodiment, the terminal acquires the first iris information at least including the first iris contraction information. A specific implementation of acquiring the first iris contraction information is described as follows. After the intensity-variable light signal generated at block S102 is projected on the iris, the iris is stimulated by the intensity-variable light signal. When there are lights, the iris is in a contraction state, and when there is no light, the iris is in a dilation state. With a constant flashing of the intensity-variable light signal, the iris contracts or dilates continuously and the first iris contraction information is generated, in which first iris contraction information includes the first iris contraction activity. In this embodiment, data to be signed-for and confirmed and other data are represented by the first iris contraction information, thereby providing a brand-new method for representing data using changes of a biological feature.

As an alternative implementation of the present embodiment, image information generated by performing an image collection on the first iris contraction activity via an image collecting component is acquired and stored by the terminal. The image collecting component may be configured inside of the terminal, or connected to the terminal externally, which will not be limited in the present embodiment. Any component having functions of the image collecting component of the present embodiment falls within the protection scope of the present disclosure. Preferably, the image collecting component may be set inside of the terminal. For example, a camera configured on a mobile phone may be regarded as the image collecting component. By regarding the camera on the mobile phone as the image collecting component, no additional image collecting component will be needed, such that it may reduce the cost have advantages of convenience and efficiency by setting the image collecting component in the terminal. In addition, the image information of the first iris contraction activity acquired by the terminal may be a video or an image, which will not be limited herein. Since the iris is regarded as a unique and constant biological feature of a human, by using the image collecting component to acquire and store the iris contraction activity, the collected iris contraction activity may be stored as an evidence. Thus, on one hand the data may be represented by the iris contraction and stored, and on the other hand it may be prevented the user from denying a signing for, a confirming operation or the like.

At block S104, the terminal acquires second iris information at least including second iris contraction information.

The second iris information may be the same as or different from the first iris information. When the second iris information is different from the first iris information, the second iris information may be acquired from other terminals via wireless transmission (such as, Bluetooth, wife, 2G, 3G, 4G, NFC or optical communication) or wired transmission (such as, USB transmission or audio interface transmission).

At block S105, the terminal extracts second data from the second iris contraction information according to a preset rule.

Regarding the specific implementation, reference can be made to the implementation of the terminal extracting the first data from the first iris contraction information according to a preset rule described in a second embodiment. In addition, the second iris information may further include second iris feature information. After the terminal acquires the second iris feature information, legality of the second iris feature information may be verified. The terminal in this embodiment not only acquires iris information, but also performs a processing on the iris information to extract data and/or to verify legality of the iris feature information.

With the method for acquiring information using a biological feature, data may be represented by using the biological feature, and the data may be embedded into the biological feature. The user may complete operations including confirming and signing-for data information by receiving an intensity-variable light signal to be irradiated on the iris. Moreover, the data embedded in the biological feature may be stored as evidence. In other words, an executive subject (the user) of the operations including confirming, signing-for and the like and the confirmed and signed-for content are stored in association manner, thereby preventing the user from denying the confirmed and signed-for content.

Second Embodiment

Figure 3:
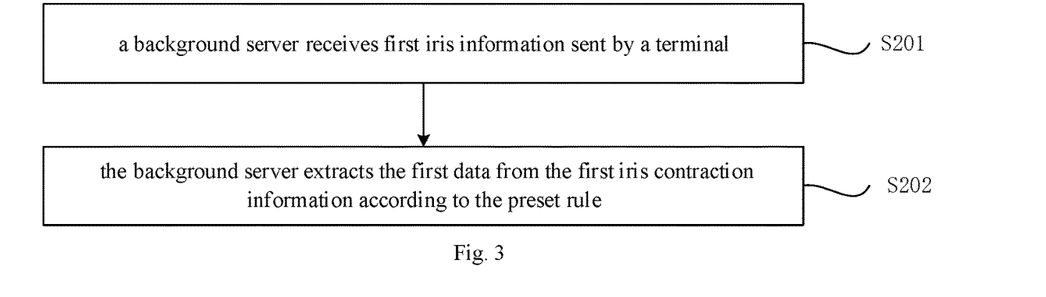
FIG. 3 is a flow chart of a method for extracting information using a biological feature provided by a second Embodiment of the present disclosure.

FIG. 3 is a flow chart of a method for extracting information using a biological feature provided by the present embodiment. As shown in FIG. 3, the method includes following acts (S201-S202).

At block S201, a background server receives first iris information sent by a terminal.

In this embodiment, the terminal may acquire the first iris information by implementation described in the first Embodiment. The first iris information at least includes first iris contraction information. After the terminal acquires the first iris information, the terminal sends the first iris information to the background server via wireless transmission or wired transmission, and the background server receives the first iris information sent by the terminal.

At block S202, the background server extracts the first data from the first iris contraction information according to the preset rule.

In a specific application, after the background server receives the first iris contraction information, the background server may identify an iris state by an image identification algorithm. The image identification algorithm is not limited in the present embodiment. Any image identification algorithm able to identify the iris state falls within the protection scope of the present disclosure. When the background server identifies that the iris state is "contraction, dilating, dilation, contraction, dilation, contraction, contraction, dilation, contraction, dilation", and the preset rule in the background server is that "dilation" represents logic "0", and "contraction" represents logic "1", the first data "1001011010" may be extracted from the iris state "contraction, dilation, dilation, contraction, dilation, contraction, contraction, dilation, contraction, dilation". When the background server identifies that the iris state is "contraction, dilation, contraction, contraction, dilation, dilation, dilation, contraction, contraction, dilation", and the preset rule in the background server is that "the iris remaining contraction or dilation" represents logic "1", "the iris state turning from dilation to contraction or from contraction to dilation" represents logic "0", if a preset initial iris state is "contraction", a first identified iris state is "contraction", which indicates "the iris remaining contraction" with respect to the initial iris state, thus it represents logic "1", if a second identified iris state is "dilation", which indicates "the iris state turning from contraction to dilation" with respect to the first iris state "contraction", thus it represents logic "0", and so on. Therefore, the first data "1001011010" may be extracted from the iris state "contraction, dilation, contraction, contraction, dilation, dilation, dilation, contraction, contraction, dilation". In addition, when the background server identifies the iris state as "sharply contraction, partly contraction, partly contraction, dilation, sharply contraction, sharply contraction", and the preset rule in the background server is that "sharply contraction" represents logic "2", "partly contraction" represents logic "1", and "dilation" represents logic "0", the ternary-encoded first data "211022" may be acquired by the background server. Alternatively, the background server may transform the ternary-encoded first data to a binary representation, i.e., the first data "1001011010" may be extracted. By extracting the first data from the iris contraction information, a brand-new method for acquiring data from changes of a biological feature is provided. In other words, the content confirmed and signed-for by the operations including confirming, signing-for and the like can be extracted from the biological feature that data is embedded in, thereby preventing the user from denying the confirmed and signed-for content.

As an alternative implementation of the present embodiment, the first iris information further includes the iris feature information. The iris feature information is formed at a fetal development stage and remains unchanged in a whole life period. Everyone's iris feature information is distinct. Therefore, the iris feature information is unique. After the background server receives the iris feature information sent by the terminal, legality of the iris feature information is verified. The specific implementation is described below. The background server may compare the iris feature information with pre-stored iris feature information and determine whether they are the same, if yes, it indicates that the iris feature information is legal, otherwise, the iris feature information is illegal. By verifying whether the iris feature information is legal, operations such as confirming or signing-for performed by lawbreakers may be prevented. In addition, the iris feature information received by the background server may be stored as evidence, thereby avoiding denying of the operational behaviors such as confirming and signing-for which are already done.

As an alternative implementation of the present embodiment, after the background server verifies the legality of the iris feature information, the verification result is sent to the terminal. For example, after the background server verifies that the iris feature information is illegal, the background server may send the verification result to the terminal in a wired or wireless manner. After the terminal receives the result indicating that the iris feature information is illegal, the user of the terminal is reminded in an alarming or displaying manner. By returning the verification result to the terminal, it is convenient for the user of the terminal to confirm whether the owner of the iris is legal in time.

As an alternative implementation of the present embodiment, before the background server extracts the first data from the first iris contraction information according to the preset rule, the background server receives the reference iris contraction information sent by the terminal, and the background server computes a correspondence between the reference data and the reference iris contraction activity according to the reference data and the reference iris contraction information. The reference data may be pre-stored in the background server, or may be generated after a negotiation between the terminal and the background server, which is not be limited in the present embodiment. In order to ensure an accuracy of extracting data, the reference data used by the background server are the same as that used by the terminal. The implementation of generating the correspondence between the reference data and the reference iris contraction activity will be illustrated below. A ternary representation of the reference data generated after the negotiation between the background server and the terminal is "012012". Before the terminal controls the light source to generate the intensity-variable light signal according to the first data, the terminal may control the light source to generate the reference light signal according to the reference data "012012". The reference light signal is an intensity-variable signal. The reference light signal stimulates the iris to generate the reference iris contraction information. The terminal acquires the reference iris contraction information and sends it to the background server. After the background server receives the reference iris contraction information sent by the terminal, a diameter of a pupil in the received reference iris contraction activity can be identified by the image identification algorithm, which may be "4 mm, 3 mm, 2 mm, 4 mm, 3 mm, 2 mm". The reference data in the background server and the reference data in the terminal are both "012012". Therefore, the correspondence between the reference data and the iris contraction activities established according to the identified diameter of the pupil and the reference data may be described as follows. When the diameter of the pupil is 4 mm, the reference data is logic "0"; when the diameter of the pupil is 3 mm, the reference data is logic "1"; when the diameter of the pupil is 2 mm, the reference data is logic "2". By establishing the correspondence between the reference data and the iris contraction activity, it is convenient for the background server to determine the logic data represented by different iris contraction degrees and different iris dilation degrees. In addition, the correspondence between the reference data and the iris contraction activity further includes a correspondence between the reference data and an activity range of the iris contraction activity. In detail, the activity range of the iris contraction activity may be a value range of diameter of the pupil of the user. For example, when the diameter of the pupil of the user falls within a value range [4.2 mm, 3.8 mm), the reference data is logic "0", when the diameter of the pupil of the user falls within a value range [3.4 mm, 3.2 mm), the reference data is logic "1", when the diameter of the pupil of the user falls within a value range [2.5 mm, 2.3 mm), the reference data is logic "2". By establishing the correspondence between the reference data and the activity range of the iris contraction activity, it may be prevented that some iris contraction degrees may be not identified under a precise identification.

As an alternative implementation of the present embodiment, different users may set different correspondences between the reference data and the iris contraction activities. Specifically, the iris contraction activity may be represented by a size of the user's pupil. For example, the correspondence between the reference data and the iris contraction activity of the user A may be set as follows. When the diameter of the pupil is 4 mm, the reference data is logic "0"; when the diameter of the pupil is 3 mm, the reference data is logic "1"; when the diameter of the pupil is 2 mm, the reference data is logic "2". The correspondence between the reference data and the iris contraction activity of the user B may be set as follows. When the diameter of the pupil is 3.6 mm, the reference data is logic "0"; when the diameter of the pupil is 2.8 mm, the reference data is logic "1"; when the diameter of the pupil is 2.2 mm, the reference data is logic "2". Of course, the correspondence between the reference data and the iris contraction activity may further include a correspondence between the reference data and an activity range of the iris contraction activity. Different users may set different correspondences between the reference data and the activity ranges of the iris contraction activities. Specifically, the activity range of the iris contraction activity may be a value range of the diameter of the pupil of the user. For example, the correspondence between the reference data and the activity range of the iris contraction activity of the user A may be set as follows. When the diameter of the pupil is within a value range of [4.2 mm, 3.8 mm), the reference data is logic "0"; when the diameter of the pupil is within a value range of [3.4 mm, 3.2 mm), the reference data is logic "1"; when the diameter of the pupil is within a value range of [2.5 mm, 2.3 mm), the reference data is logic "2". The correspondence between the reference data and the activity range of the iris contraction activity of the user B may be set as follows. When the diameter of the pupil is within a value range of [3.7 mm, 3.5 mm), the reference data is logic "0"; when the diameter of the pupil is within a value range of [2.9 mm, 2.7 mm), the reference data is logic "1"; when the diameter of the pupil is within a value range of [2.3 mm, 2.1 mm), the reference data is logic "2". Preferably, the iris feature information and the correspondence between the reference data and the iris contraction activity may be stored correspondingly. The background server may search for the correspondence between the reference data and the iris contraction activity according to the iris feature information. By storing the iris feature information and the correspondence in an association manner, different users may set different correspondences between the reference data and the iris contraction activities. Of course, other methods may be used to set different correspondences between the reference data and the iris contraction activities by different users, which will not be limited herein. By setting different correspondences between the reference data and the iris contraction activities by different users, an extracting error caused by different users using same reference data may be avoided.

With the method for acquiring information using a biological feature provided by the present embodiment, data may be extracted and recovered from the biological feature that the data is embedded in. In other words, the content confirmed and signed-for by confirming and signing-for operations may be extracted from the biological feature that the data is embedded in, thereby preventing the user from denying the confirmed and signed-for content.

Third Embodiment

Figure 4:
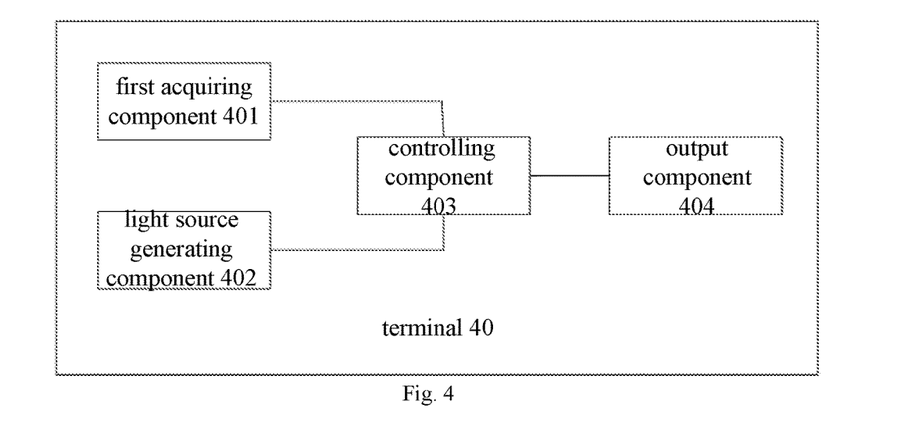
FIG. 4 is a structure diagram of a terminal provided by a third Embodiment of the present disclosure.

FIG. 4 is a structure diagram of a terminal provided by the present embodiment. As shown in FIG. 4, the terminal 40 may include: a first acquiring component 401, a light source generating component 402, a controlling component 403 and an output component 404.

The first acquiring component 401 is configured to acquire first data. The light source generating component 402 is configured to generate a light source. The controlling component 403 is configured to control the light source to generate an intensity-variable light signal according to the first data. The output component is configured to project the intensity-variable light signal on an iris. The first acquiring component 401 is further configured to acquire first iris information at least including first iris contraction information, in which the first iris contraction information is generated by the iris according to the intensity-variable light signal and includes a first iris contraction activity.

In this embodiment, the first data acquired by the first acquiring component 401 is data to be represented by an iris contraction activity. The first data may be any one of a time, a site, character (such as a name), order information, trade information, signature data and any combination thereof, or may be a characteristic value acquired by performing computation on any one of the time, the site, the character, the order information, the trade information, the signature data and any combination thereof, or may be data generated by combining the characteristic value with any one of the time, the site, the character, the order information, the trade information, the signature data and any combination thereof. Any data represented by the iris contraction activity may be determined as the first data, which will not be limited in this embodiment. Various methods may be used to compute the characteristic value. For example, N-digit data is to be computed in the present disclosure, first X digits in the data may be selected as the characteristic value, where 1≤X≤N. Alternatively, Y digits in the data may be computed as the characteristic value by hash algorithm or MAC algorithm, where 1≤Y≤N. Efficiency may be improved by selecting the characteristic value as the first data, such that a light simulation to the iris may be reduced when there are too many digits in the first data.

As an alternative implementation, the first data may also be numbers of different events. For example, in an event of fetching an express delivery, the first data may be 1; in an event of shopping, the first data may be 2; in an event of hailing a cab, the first data may be 3. Of course, the first data may be numbers of application scenes of different events, in which the number may be represented by a number corresponding to event plus a number corresponding to application scene. For example, in an application scene of fetching an SF express delivery, the first data may be 11; in an application scene of fetching a YTO express delivery, the first data may be 12; in an application scene of fetching a ZTO express delivery, the first data may be 13; in an application scene of shopping at Kade Mall, the first data may be 21; in an application scene of shopping at Wu-Mart, the first data may be 22; in an application scene of shopping at Wal-Mart, the first data may be 23. In a case of numbering different events and/or application scenes with digits, it is convenient to confirm the kind of event on which operations including confirming, signing-for and the like are performed by using the first data.

In this embodiment, the light source generated by the light source generating component 402 may be infrared light, visible light or white light. The light source generating component 402 may be an infrared lamp or a flashlight, which is not limited herein. Any light source generating component 402 which generates light source causing an iris contraction and dilation falls within the protection scope of the present disclosure. Preferably, a flashlight configured on a terminal such as a mobile phone may be regarded as the light source generating component 402, in this case, no additional light generating source device is needed for the terminal such as the mobile phone, thereby reducing the cost.

In this embodiment, the controlling component 403 may generate the intensity-variable light signal by modulating the first data on the light source. Of course, the controlling component 403 may encode the first data firstly and modulate the encoded first data on the light source to generate the intensity-variable light signal. After the controlling component 403 generates the intensity-variable light signal, the intensity-variable light signal may be projected on the iris by the output component 404. The iris is stimulated by the intensity-variable light signal and the first iris contraction information is generated. The first acquiring component 401 is further configured to acquire the first iris information. The first iris information at least includes the first iris contraction information. With the terminal provided by the present embodiment, the iris may be stimulated and changed, and data information represented by the iris contraction information may be acquired.

Figure 5:
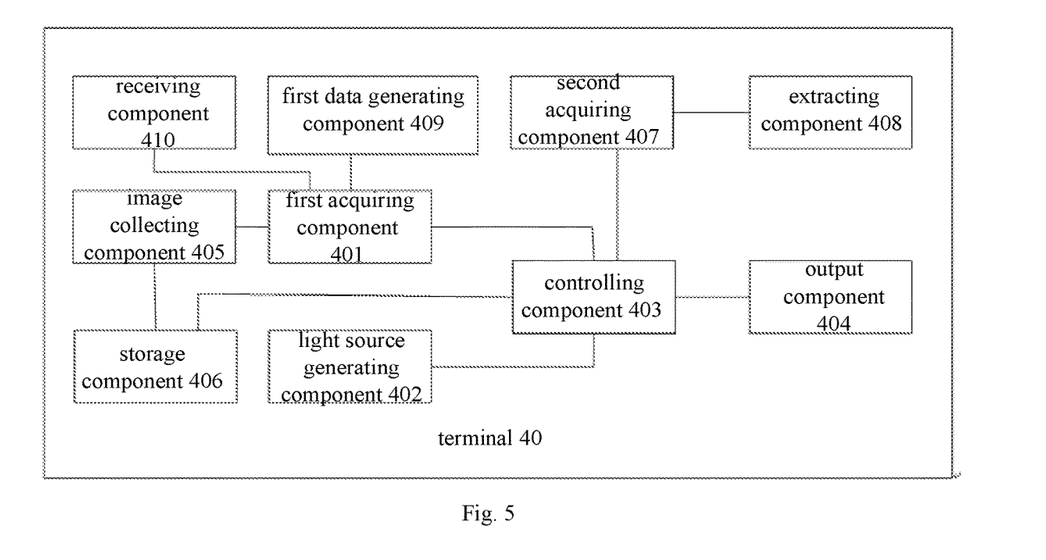
FIG. 5 is a structure diagram of another terminal provided by the third Embodiment of the present disclosure.

As an alternative implementation of this embodiment, the first acquiring component 401 acquires the first iris information according to image information generated by performing an image collection on the first iris contraction activity by an image collecting component 405. As shown in FIG. 5, the image collecting component 405 may be set inside of the terminal. After the image collecting component 405 performs the image collection on the first iris contraction activity to generate the image information, a storage component 406 may store the image information collected by the image collecting component 405. The first acquiring component 401 acquires the image information of the first iris contraction activity from the image collecting component 405. Of course, the image collecting component 405 may be set outside of the terminal. The image collecting component 405 may be connected to the terminal 40 in a wired or wireless manner. The image collecting component 405 sends the collected image information of the first iris contraction activity to the first acquiring component 401 in a wired or wireless transmission manner, and the first acquiring component 401 acquires the image information of the first iris contraction activity. By acquiring and storing the image information of the first iris contraction activity by the first acquiring component 401, on one hand the data may be represented by the iris contraction and stored, and on the other hand it may be prevented the user from denying the operational behaviors such as signing-for, confirming or the like which are already done.

As an alternative implementation of the present embodiment, as shown in FIG. 5, the terminal 40 may further include a second acquiring component 407 and an extracting component 408. The second acquiring component 407 is configured to acquire second iris information at least including second iris contraction information. The extracting component 408 is configured to extract second data from the second iris contraction information according to a preset rule. In a specific implementation, the second iris contraction information may be the same as or different from the first iris contraction information. The second acquiring component 407 may acquire the second iris information in the same manner as the first acquiring component 401 acquiring the first iris information. Alternatively, the second iris information may be acquired by other terminals and sent to the second acquiring component 407, and the second acquiring component 407 acquires the second iris information sent by other terminals. After the second acquiring component 407 acquires the second iris information, the extracting component 408 extracts second data from the second iris contraction information according to the preset rule, regarding the implementation of extracting component 408, reference may be made to the implementation of the extracting component 502 extracting the first data from the first iris contraction information according to a preset rule described in a fourth embodiment. Further, the first iris information may further include second iris feature information. After the second acquiring component 407 acquires the second iris feature information, legality of the second iris feature information may be verified. With the extracting component 408 set in the terminal, the terminal may be used to process the iris information, so as to extract data and/or to verify the legality of the iris feature information.

As an alternative implementation of the present embodiment, as shown in FIG. 5, the first data may be generated by a first data generating component 409, and the first acquiring component 401 acquires the first data from the first data generating component 409. Preferably, a receiving component 410 may be used to receive the first data sent by a background server, and the first acquiring component 401 acquires the first data from the receiving component 410. By receiving the first data sent by the background server with the receiving component 410, malicious tempering with the first data can be avoided.

As an alternative implementation of the present embodiment, the controlling component 403 is further configured to control the light source to generate a reference light signal according to reference data. The reference data may be data generated by a negotiation between the first acquiring component 401 and the background server, or may be data stored in the storage component 406, but the above reference data is the same as the reference data in the background server. The implementation of the controlling component 403 controlling the light source to generate the reference light signal according to the reference data is the same as that of the controlling component 403 controlling the light source to generate the intensity-variable light signal according to the first data, which is not described herein. It should be understood that the reference light signal is an intensity-variable light signal. After the controlling component 403 controls the light source to generate the reference light signal, the output component 404 projects the reference light signal on the iris. The first acquiring component 401 is further configured to acquire the reference iris information, the reference iris information at least includes the reference iris contraction information. The reference iris contraction information acquired by the terminal 40 may be regarded as reference information to calibrate the iris contraction activity in a process of identifying the first iris contraction information.

With the terminal provided by the present embodiment, data represented by a biological feature may be acquired, thereby preventing the user from denying the confirmed or signed-for content.

Fourth Embodiment

Figure 6:
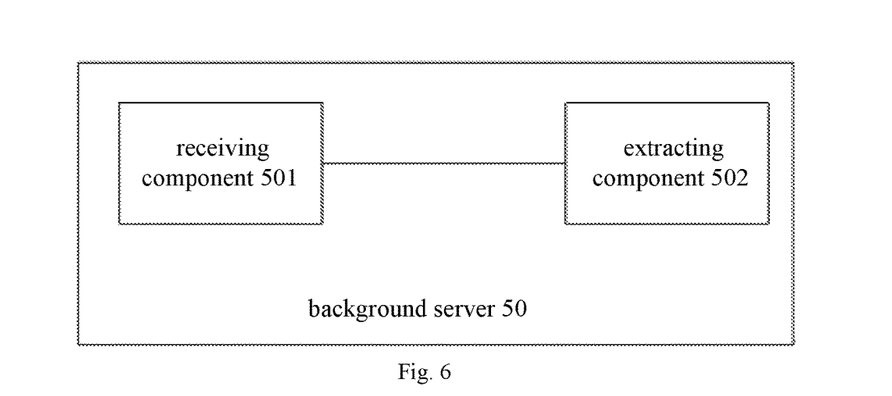
FIG. 6 is a structure diagram of a background server provided by a fourth Embodiment of the present disclosure.

FIG. 6 is a structure diagram of a background server provided by the present embodiment. As shown in FIG. 6, the background server 50 includes a receiving component 501 and an extracting component 502. The receiving component 501 is configured to receive first iris information sent by a terminal 40, in which the first iris information at least includes first iris contraction information. The extracting component 502 is configured to extract first data from the first iris contraction information according to a preset rule.

In this embodiment, the terminal 40 may acquire the first iris information in a manner described in the first embodiment. The terminal 40 sends the first iris information to the background server 50 after the first iris information is acquired. The receiving component 501 in the background server 50 receives the first iris information sent by the terminal 40. The first iris information at least includes the first iris contraction information. The implementation of the extracting component 502 extracting the first data from the first iris contraction information according to a preset rule may be described as follows. Firstly, the extracting component 502 identifies an iris state (for example, a dilation state or a contraction state of the iris) from the iris contraction information using an algorithm such as an image identification algorithm. A specific image identification algorithm is not limited herein, as long as the iris state can be identified. When the iris state identified by the extracting component 502 is "contraction, dilation, dilation, contraction, dilation, contraction, contraction, dilation, contraction, dilation", and the preset rule is that "dilation" represents logic "0", and "contraction" represents logic "1", the first data "1001011010" may be extracted. When the iris state identified by the extracting component 502 is "contraction, dilation, contraction, contraction, dilation, dilation, dilation, contraction, contraction, dilation", and the preset rule is that "the iris remaining contraction or dilation" represents logic "1", "the iris state turning from dilation to contraction or from contraction to dilation" represents logic "0", if a preset initial iris state is "contraction", a first iris state extracted by the extracting component 502 is "contraction", which indicates "the iris remaining contraction" with respect to the initial iris state, thus it represents logic "1", if a second iris state extracted by the extracting component 502 is "dilation", which indicates "the iris state turning from contraction to dilation" with respect to the first iris state "contraction", thus it represents logic "0", and so on. Therefore, the first data "1001011010" may be extracted. When the iris state identified by the extracting component 502 is "sharply contraction, partly contraction, partly contraction, dilation, sharply contraction, sharply contraction", and the preset rule is that "sharply contraction" represents logic "2", "partly contraction" represents logic "1", and "dilation" represents logic "0", the ternary-represented first data "211022" is extracted. Alternatively, the extracting component 502 may transform the ternary data to a binary data, and the first data "1001011010" may be extracted. With the background server 60 provided by the present embodiment, the first data may be extracted from the iris contraction information.

Figure 7:
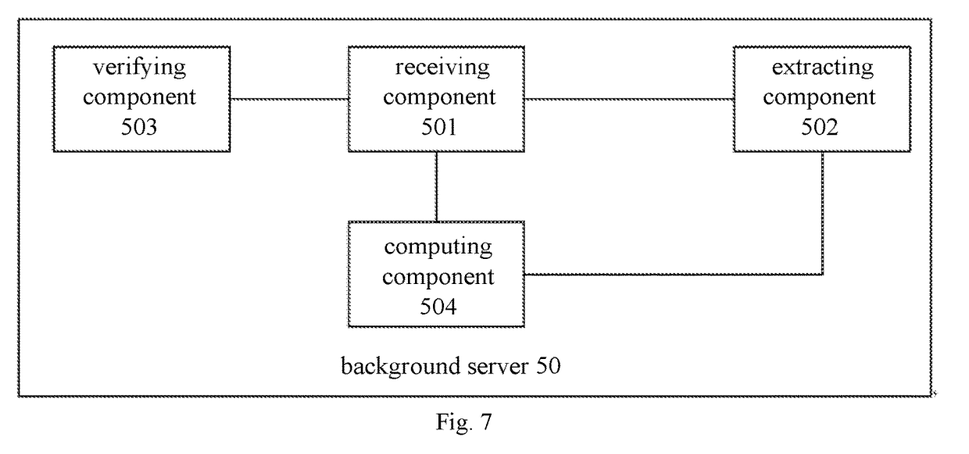
FIG. 7 is a structure diagram of another background server provided by the fourth Embodiment of the present disclosure.

As an alternative implementation of the present embodiment, as shown in FIG. 7, the background server 50 further includes a verifying component 503. The receiving component 501 receives the first iris information sent by the terminal 40. Besides the first iris contraction information, the first iris information further includes the first iris feature information. The verifying component 503 is configured to verify legality of the first iris feature information after the receiving component 501 receives the first iris feature information sent by the terminal 40. The specific implementation of the verifying component 503 verifying the legality of the first iris feature information may be described as follows. The verifying component 503 compares the iris feature information received by the receiving component 501 with pre-stored iris feature information. If the iris feature information received by the receiving component 501 is the same as the pre-stored iris feature information, the iris feature information is legal; if the iris feature information received by the receiving component 501 is different from the pre-stored iris feature information, the iris feature information is illegal. By verifying the legality of the first iris feature information, operations such as confirming or signing-for performed by lawbreakers may be prevented. In addition, the iris feature information received by the background server may be stored as evidence, thereby avoiding denying of the operational behaviors such as confirming and signing which are already done.

As an alternative implementation of the present embodiment, after the verifying component 503 verifies the legality of the iris feature information, the verification result is sent to the terminal 40. After the terminal 40 receives the result indicating that the iris feature information is illegal, the user of the terminal 40 is reminded in an alarming or displaying manner. By returning the verification result to the terminal, it is convenient for the user of the terminal to confirm whether the owner of the iris is legal in time.

As an alternative implementation of the present embodiment, as shown in FIG. 7, the background server further includes a computing component 504. The computing component 504 is configured to compute a correspondence between the reference data and the reference iris contraction activity according to the reference data and the reference iris contraction information. The reference data is the same as the reference data in the terminal 40, and the method for acquiring the reference data is the same as the method for acquiring the reference data by the terminal described in the fourth embodiment, which will not be described in detail herein. Before the receiving component 501 receives the first iris contraction information, the receiving component 501 is configured to receive reference iris contraction information. After the receiving component 501 receives the reference iris contraction information, the computing component 504 computes and generates the correspondence between the reference data and the reference iris contraction activity. When a ternary representation of the reference data is "012012", the established correspondence between the reference data and the iris contraction activity may be described as follows. When the diameter of the pupil is 4 mm, the reference data is logic "0"; when the diameter of the pupil is 3 mm, the reference data is logic "1"; when the diameter of the pupil is 2 mm, the reference data is logic "2". The extracting component 502 is configured to extract the first data from the first iris contraction information according to the correspondence between the reference data and the reference iris contraction activity. For example, after the receiving component 501 receives the first iris contraction information, the diameter of the pupil in the first iris contraction activity identified by the extracting component 502 according to image identification algorithm may be "2 mm, 3 mm, 3 mm, 4 mm, 2 mm, 2 mm", the ternary-encoded data "211022" may be extracted according to the above correspondence. By transforming the ternary-encoded data to binary data, the first data "1001011010" may be extracted. Preferably, the correspondence between the reference data and the reference iris contraction activity computed by the computing component 504 further includes a correspondence between the reference data and an activity range of the reference iris contraction activity. For example, the established correspondence between the reference data and the activity range of the iris contraction activity may be described as follows. When the diameter of the pupil is within a value range of [4.2 mm, 3.8 mm), the reference data is logic "0"; when the diameter of the pupil is within a value range of [3.4 mm, 3.2 mm), the reference data is logic "1"; when the diameter of the pupil is within a value range of [2.5 mm, 2.3 mm), the reference data is logic "2". The extracting component 502 identifies the first iris state by the image identification algorithm as the diameter of the pupil being "2.4 mm, 3.2 mm, 3.3 mm, 4.1 mm, 2.3 mm, 2.3 mm", a ternary-encoded data "211022" is extracted according to the above correspondence. By transforming the ternary-encoded data to binary data, the first data "1001011010" may be extracted. By establishing the correspondence between the reference data and the activity range of the iris contraction activity, it may be avoided that some iris contraction degrees may be not identified under a precise identification.

As an alternative implementation of the present embodiment, the background server 50 further includes a storage component, configured to store different correspondences between the reference data and the iris contraction activities of different users. Specifically, the iris contraction activity may be represented by a size of the pupil of the user. For example, the correspondence between the reference data and the iris contraction activity of the user A may be set as follows. When the diameter of the pupil is 4 mm, the reference data is logic "0"; when the diameter of the pupil is 3 mm, the reference data is logic "1"; when the diameter of the pupil is 2 mm, the reference data is logic "2". The correspondence between the reference data and the iris contraction activity of the user B may be set as follows. When the diameter of the pupil is 3.6 mm, the reference data is logic "0"; when the diameter of the pupil is 2.8 mm, the reference data is logic "1"; when the diameter of the pupil is 2.2 mm, the reference data is logic "2". Of course, the correspondence between the reference data and the iris contraction activity may further include a correspondence between the reference data and an activity range of the iris contraction activity. Different users may set different correspondences between the reference data and the activity ranges of the iris contraction activities. Specifically, the activity range of the iris contraction activity may be a value range of the diameter of the pupil of the user. For example, the correspondence between the reference data and the activity range of the iris contraction activity of the user A may be set as follows. When the diameter of the pupil is within a value range of [4.2 mm, 3.8 mm), the reference data is logic "0"; when the diameter of the pupil is within a value range of [3.4 mm, 3.2 mm), the reference data is logic "1"; when the diameter of the pupil is within a value range of [2.5 mm, 2.3 mm), the reference data is logic "2". The correspondence between the reference data and the activity range of the iris contraction activity of the user B may be set as follows. When the diameter of the pupil is within a value range of [3.7 mm, 3.5 mm), the reference data is logic "0"; when the diameter of the pupil is within a value range of [2.9 mm, 2.7 mm), the reference data is logic "1"; when the diameter of the pupil is within a value range of [2.3 mm, 2.1 mm), the reference data is logic "2". Preferably, the iris feature information and the correspondence between the reference data and the iris contraction activity may be stored correspondingly in the storage component. Thus, after the receiving component 501 receives the iris feature information, the correspondence between the reference data and the iris contraction activity corresponding to the iris feature information may be found in the storage component according to the iris feature information. By storing the iris feature information and the correspondence in an association manner, different users may set different correspondences between the reference data and the iris contraction activities. Of course, other methods may be used to set different correspondences between the reference data and the iris contraction activities by different users, which will not be limited herein. By setting different correspondences between the reference data and the iris contraction activities for different users, an extracting error caused by different users using same reference data may be avoided.

With the background server provided by the present embodiment, data may be extracted and recovered from the biological feature that the data is embedded in, thereby preventing the user from denying the confirmed or signed-for content.

Fifth Embodiment

Figure 8:
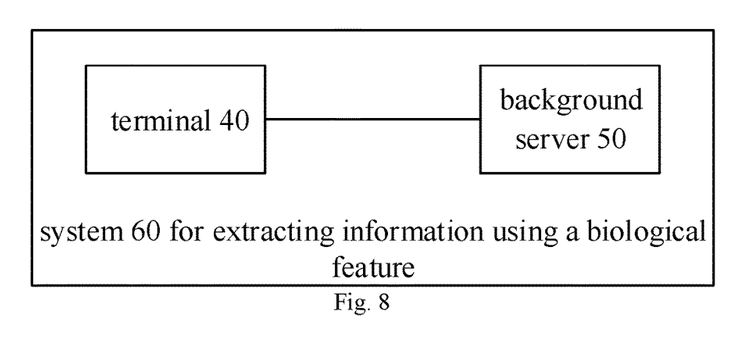
FIG. 8 is a block diagram of a system for extracting information using a biological feature provided by a fifth Embodiment of the present disclosure.

FIG. 8 is a block diagram of a system for extracting information using a biological feature provided by the present embodiment. As shown in FIG. 8, the system for extracting information using a biological feature provided by the present embodiment includes a terminal 40 and a background server 50. The terminal 40 is provided in the third embodiment of the present disclosure, and the background server 50 is provided in the fourth embodiment of the present disclosure.

The terminal 40 is configured to acquire first data, to control light source to generate an intensity-variable light signal according to the first data, to project the intensity-variable light signal on an iris, and to acquire first iris information at least including first iris contraction information, in which the first iris contraction information is generated by the iris according to the intensity-variable light signal and includes a first iris contraction activity. The terminal 40 is further configured to send the first iris information to the background server 50. The background server 50 is configured to receive the first iris information sent by the terminal, and to extract first data from the first iris contraction information according to a preset rule.

As an alternative implementation of the present embodiment, the first iris information acquired by the terminal 40 further includes first iris feature information besides the first iris contraction information. After the background server 50 receives the first iris feature information sent by the terminal 40, the background server 50 is further configured to verify legality of the first iris feature information. By verifying whether the iris feature information is legal, operations such as confirming or signing-for performed by lawbreakers may be avoided. In addition, the iris feature information received by the background server may be stored as evidence, thereby avoiding denying of the operational behaviors such as confirming and signing-for which are already done.

As an alternative implementation of the present embodiment, the terminal 40 is further configured to control the light source to generate a reference light signal according to the reference data. Preferably, the reference light signal is generated before the intensity-variable light signal is generated. After the terminal 40 controls the light source to generate the reference light signal according to reference data, the reference light signal is projected on the iris. The terminal 40 acquires reference iris contraction information, in which the reference iris contraction information is generated by the iris according to the reference light signal. The terminal 40 sends the reference iris contraction information to the background server 50. Specifically, the reference iris contraction information may be sent to the background server 50 by the terminal 40 before the first iris information is sent, or may be sent together with the acquired first iris information, which will not be limited herein. After the background server 50 receives the reference iris contraction information sent by the terminal 40, a correspondence between the reference data and the reference iris contraction activity is computed according to the reference data and the reference iris contraction information, in which the correspondence between the reference data and the reference iris contraction activity may include a correspondence between the reference data and an activity range of the reference iris contraction activity. The background server 50 is further configured to extract the first data from the first iris contraction information according to the correspondence between the reference data and the reference iris contraction activity. In addition, the correspondence between the reference data and the reference iris contraction activity includes a correspondence between the reference data and an activity range of the reference iris contraction activity. By establishing the correspondence between the reference data and the reference iris contraction activity, the received iris contraction activity may be calibrated.

With the system for extracting information using a biological feature, the data may be represented using a biological feature, and the data may also be extracted and recovered from the biological feature that the data is embedded in, thereby preventing the user from denying the confirmed and signed-for content.

Any process or method described in a flow chart or described herein in other ways may be understood to include one or more modules, segments or portions of codes of executable instructions for achieving specific logical functions or steps in the process, and the scope of a preferred embodiment of the present disclosure includes other implementations. Implementing orders which are not illustrated or discussed may be allowed, functions may be implemented in a basically simultaneous order or an adverse order according to the related functions, which should be understood by persons of ordinary skill in the art.

It should be understood that each part of the present disclosure may be realized by the hardware, software, firmware or their combination. In the above embodiments, a plurality of steps or methods may be realized by the software or firmware stored in the memory and executed by the appropriate instruction execution system. For example, if it is realized by the hardware, likewise in another embodiment, the steps or methods may be realized by one or a combination of the following techniques known in the art: a discrete logic circuit having a logic gate circuit for realizing a logic function of a data signal, an application-specific integrated circuit having an appropriate combination logic gate circuit, a programmable gate array (PGA), a field programmable gate array (FPGA), etc.

Persons of ordinary skill in the art shall understand that all or parts of the steps in the above exemplifying method of the present disclosure may be achieved by commanding the related hardware with programs. The programs may be stored in a computer readable storage medium, and the programs include one or a combination of the steps in the method embodiments of the present disclosure when run on a computer.

In addition, each function cell of the embodiments of the present disclosure may be integrated in a processing module, or these cells may be separate physical existence, or two or more cells are integrated in a processing module. The integrated module may be realized in a form of hardware or in a form of software function modules. When the integrated module is realized in a form of software function module and is sold or used as a standalone product, the integrated module may be stored in a computer readable storage medium.

The storage medium mentioned above may be read-only memories, magnetic disks or CD, etc.

Reference throughout this specification to "an embodiment," "some embodiments," "one embodiment", "another example," "an example," "a specific example," or "some examples," means that a particular feature, structure, material, or characteristic described in connection with the embodiment or example is included in at least one embodiment or example of the present disclosure. Thus, the appearances of the phrases such as "in some embodiments," "in one embodiment", "in an embodiment", "in another example," "in an example," "in a specific example," or "in some examples," in various places throughout this specification are not necessarily referring to the same embodiment or example of the present disclosure. Furthermore, the particular features, structures, materials, or characteristics may be combined in any suitable manner in one or more embodiments or examples.

Although explanatory embodiments have been shown and described, it would be appreciated by persons of ordinary skill in the art that the above embodiments cannot be construed to limit the present disclosure, and changes, alternatives, and modifications can be made in the embodiments without departing from scope of the present disclosure.

What is claimed is:

1. A method for acquiring information using a biological feature, comprising:
   acquiring first data by a terminal;
   controlling, by the terminal, a light source to generate an intensity-variable light signal according to the first data, and projecting the intensity-variable light signal on an iris;
   acquiring, by the terminal, first iris information at least comprising first iris contraction information, wherein the first iris contraction information is generated by the iris according to the intensity-variable light signal and comprises a first iris contraction activity;
   acquiring, by the terminal, second iris information at least comprising second iris contraction information; and
   extracting, by the terminal, second data from the second iris contraction information according to a preset rule.

2. The method according to claim 1, wherein acquiring by the terminal the first iris information comprises:
   acquiring and storing, by the terminal, image information generated by performing an image collection on the first iris contraction activity via an image collecting component.

3. The method according to claim 2, wherein controlling, by the terminal, a light source to generate an intensity-variable light signal according to the first data comprises at least one of:
   modulating, by the terminal, the first data on the light source in a preset modulation mode, so as to generate the intensity-variable light signal; and
   encoding, by the terminal, the first data to generate an encoded signal of the first data, and modulating the encoded signal on the light source in the preset modulation mode, so as to generate the intensity-variable light signal.

4. The method according to claim 1, wherein controlling, by the terminal, a light source to generate an intensity-variable light signal according to the first data comprises at least one of:
   modulating, by the terminal, the first data on the light source in a preset modulation mode, so as to generate the intensity-variable light signal; and
   encoding, by the terminal, the first data to generate an encoded signal of the first data, and modulating the encoded signal on the light source in the preset modulation mode, so as to generate the intensity-variable light signal.

5. The method according to claim 4, wherein the preset modulation mode refers to an intensity modulation mode.

6. The method according to claim 1, wherein the first data comprises at least one of: a time, a site, a character, order information, trade information, signature data and a characteristic value acquired by performing computation on at least one of the time, the site, the character, the order information, the trade information and the signature data.

7. The method according to claim 6, wherein when the computation is performed on N-digit data, the first X digits in the N-digit data is selected as the characteristic value, where $1 \leq X \leq N$.

8. The method according to claim 6, wherein when the computation is performed, Y digits data is computed as the characteristic value by one of hash algorithm and MAC algorithm, where $1 \leq Y \leq N$.

9. The method according to claim 1, wherein acquiring the first data by the terminal comprises at least one of:
   generating the first data by the terminal; and
   receiving, by the terminal, the first data sent by a background server.

10. The method according to claim 1, wherein before controlling by the terminal the light source to generate the intensity-variable light signal according to the first data, the method further comprises:
    controlling, by the terminal, the light source to generate a reference light signal according to reference data;
    projecting, by the terminal, the reference light signal on the iris after the terminal controls the light source to generate the reference light signal according to the reference data; and
    acquiring, by the terminal, reference iris contraction information, in which the reference iris contraction information is generated by the iris according to reference light signal and comprises a reference iris contraction activity.

11. The method according to claim 10, wherein the reference light signal is a flashing light signal; and when the reference light signal is projected on the iris, the iris is in a contraction state if there is light projected on the iris and the iris is in a dilation state if there is no light projected on the iris.

12. A terminal, comprising:
    a first acquiring component, configured to acquire first data;
    a light source generating component, configured to generate a light source;
    a controlling component, configured to control the light source to generate an intensity-variable light signal according to the first data;
    an output component, configured to project the intensity-variable light signal on an iris, wherein the first acquiring component is further configured to acquire first iris information at least comprising first iris contraction information, in which the first iris contraction information is generated by the iris according to the intensity-variable light signal and comprises a first iris contraction activity;
    wherein the terminal further comprises:
    a second acquiring component, configured to acquire second iris information at least comprising second iris contraction information; and
    an extracting component, configured to extract second data from the second iris contraction information according to a preset rule.

13. The terminal according to claim 12, further comprising: a storage component, wherein, the first acquiring component is further configured to acquire image information generated by performing an image collection on the first iris contraction activity via an image collecting component; and the storage component is configured to store the image information.

14. The terminal according to claim 13, further comprising at least one of:
a first data generating component, configured to generate the first data; and
a receiving component, configured to receive the first data sent by a background server.

15. The terminal according to claim 12, further comprising at least one of:
a first data generating component, configured to generate the first data; and
a receiving component, configured to receive the first data sent by a background server.

16. The terminal according to claim 12, wherein,
the controlling component is further configured to control the light source to generate a reference light signal according to reference data;
the output component is further configured to project the reference light signal on the iris; and
the first acquiring component is further configured to acquire reference iris information at least comprising reference iris contraction information.

* * * * *